(12) United States Patent
Wong et al.

(10) Patent No.: US 6,565,615 B1
(45) Date of Patent: May 20, 2003

(54) DYE COMPOSITIONS

(75) Inventors: Michael Y. M. Wong, Easton, CT (US); Stanley Pohl, Scarsdale, NY (US)

(73) Assignee: Clairol Incorporated, Stamford, CT (US)

( * ) Notice: Subject to any disclaimer, the term of this patent is extended or adjusted under 35 U.S.C. 154(b) by 0 days.

(21) Appl. No.: 09/248,387

(22) Filed: Feb. 12, 1999

Related U.S. Application Data

(63) Continuation-in-part of application No. 08/972,979, filed on Nov. 19, 1997, now abandoned.

(51) Int. Cl.⁷ .................................................. A61K 7/13
(52) U.S. Cl. ...................... 8/408; 8/406; 8/410; 8/412; 8/416; 8/421; 8/435
(58) Field of Search ............................ 8/408, 421, 424, 8/435, 416, 410, 412, 405

(56) References Cited

U.S. PATENT DOCUMENTS

| | | | |
|---|---|---|---|
| 4,507,280 A | * 3/1985 | Pohl et al. | |
| 4,840,639 A | * 6/1989 | Husemeyer et al. | 8/410 |
| RE33,786 E | * 1/1992 | Pohl et al. | |
| 5,104,412 A | * 4/1992 | Rose et al. | 8/405 |
| 5,344,463 A | * 9/1994 | Chan et al. | 8/408 |
| 5,514,188 A | * 5/1996 | Cotteret et al. | 8/412 |
| 5,529,584 A | * 6/1996 | Audousset et al. | 8/412 |
| 5,538,516 A | * 7/1996 | Audousset et al. | |
| 5,595,573 A | * 1/1997 | Audousset et al. | |
| 5,599,353 A | * 2/1997 | Cotteret et al. | 8/412 |
| 5,645,610 A | * 7/1997 | Balzer et al. | 8/411 |
| 5,703,266 A | * 12/1997 | Lagrange et al. | 558/408 |
| 5,735,908 A | * 4/1998 | Cotteret et al. | |
| 5,743,919 A | * 4/1998 | Moeller et al. | 8/409 |
| 5,849,042 A | * 12/1998 | Lim et al. | 8/408 |
| 5,865,854 A | * 2/1999 | Lim et al. | |
| 5,961,666 A | * 10/1999 | Lim et al. | 8/408 |
| 5,964,898 A | * 10/1999 | Cotteret et al. | 8/410 |
| 5,980,584 A | 11/1999 | Lim et al. | 8/408 |
| 6,001,136 A | * 12/1999 | Audousset | 8/412 |

FOREIGN PATENT DOCUMENTS

| | | |
|---|---|---|
| EP | 0 920 853 A1 | 6/1999 |
| EP | 0 999 203 A1 | 5/2000 |
| GB | 2239265 * | 6/1991 |

OTHER PUBLICATIONS

Engliah language translation of EP 182,187, Wella, pp. 1–18, May 1986.*
Combined Search & Examination Report under Sections 17 and 18(3) Feb. 26, 2001.
Combined Search & Examination Report under Sections 17 and 18(3) Feb. 29, 2001.
Neact Journal, N.E. Assoc. of Chemistry Teachers, vol. 11 No. 1, Fall–Winter 1992, pp. 14–16. (no month available).
CRC, Handbook of Solubility Parameters and Other Cohesion Parameters, Barton, A.; pp. 149 and 444–445 (no date available).

* cited by examiner

Primary Examiner—Margaret Einsmann
(74) Attorney, Agent, or Firm—Charles J. Zeller

(57) ABSTRACT

A hair dye composition comprising a primary intermediate, a coupler and oxidant and water wherein the primary intermediate is a compound of the formula I or II

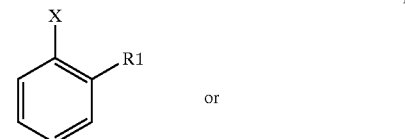

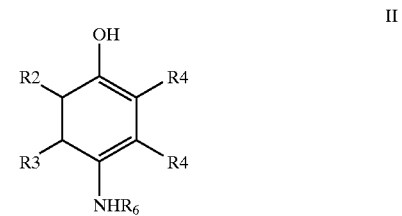

with the proviso that when the primary intermediate has the formula II, the coupler has the formula III

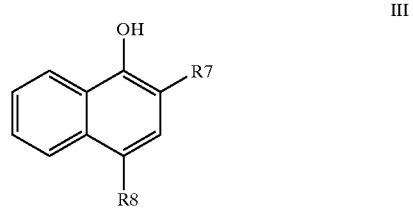

18 Claims, No Drawings

DYE COMPOSITIONS

RELATED APPLICATIONS

This is a continuation in part of application Ser. No. 08/972, 979 filed Nov. 19, 1997, now abandoned.

FIELD OF INVENTION

This invention relates to aqueous oxidative, hair coloring compositions, which produce a vivid, intense dyeout having superior wash fastness and high resistance to light fading.

BACKGROUND OF INVENTION

Modern hair dyeing methodology has developed from its initiation in the 1950's to the point where, following shampoos and conditioners, today it is the third largest product type in the hair care category.

The most commonly used method of dyeing hair, particularly human hair, is oxidative dyeing in which a mixture of essentially colorless aromatic compounds, generally diaminobenzenes, dihydroxy benzenes and aminophenols, are converted by chemical reactions, that are well known to those skilled in the art, to a blend of colored compounds within the hair fibers. Shortly before use, the colorless aromatic compounds, in a suitable base formulation, are normally mixed with hydrogen peroxide or other strong oxidizing agents. The colored compounds or dyes are typically formed by oxidative coupling between primary intermediates (usually p-phenylenediamines or p-aminophenols) and couplers which are phenols, resorcinols, m-aminophenols or related cyclic compounds. Various shades are developed by using mixtures containing more than one of both the intermediate and the coupler.

Because of their low molecular weights and water solubility the primary intermediates and couplers diffuse easily into the hair where the coupling reaction takes place. The colored products developed by oxidation remain trapped in the hair because of their higher molecular weights, relative insolubility in water and absorptive affinity to the internal hair surface. This is the basis for permanent tints and toners which ideally last for the life of the hair and are relatively unaffected by light, shampooing and perspiration.

The practice of oxidative hair coloring is well known. Typically, it involves the use of a two-part system. One part, the dye component, contains at least one primary intermediate and at least one coupler. Before use, the dye component is mixed with a second part, which is a developer formulation containing an oxidizing agent. The developer oxidizes the primary intermediate to a quinone imine. This, in turn, reacts with a coupler to form a colored compound.

There are a number of primary intermediates and couplers that are used in the practice of oxidative dyeing of hair. Based on their frequency of use, the most useful primary intermediates, are the following: p-phenylenediamine, p-toluenediamine, p-amino-phenol, 2-chloro-p-phenylenediamine and 2-methoxy-p-phenylene-diamine. The most useful couplers, based on their frequency of use, are the following: resorcinol, 1-napthol, 2-methyl-resorcinol, m-aminophenol, 2,4-diaminophenolethanol, 5-methyl-3-aminophenol, 4-methyl-3-aminophenol and m-phenylenediamine. Many combinations of primary intermediates and couplers are known and described. The following United States patents contain some representative examples:

| 5,032,138; | | 5,393,305; |
|---|---|---|
| 5,344,463; | | 5,609,651; |
| 5,393,305; | and | 5,843,193; |

Although hydrogen peroxide is the most widely employed oxidant, other oxidizing agents are known and sometimes used. These include alkali and alkaline earth metal chlorites, which are described in U.S. Pat. No. 5,032,138. Other oxidizing agents employed in oxidative hair coloring include urea peroxide, melamine peroxide and perborates and percarbonates such as sodium perborate and sodium percarbonate.

All of the above-identified patents are incorporated herein by reference in their entirety.

To be useful for coloring hair; oxidative dye formulations should meet at least the following conditions:

1. They must provide a range of color shades that are acceptable to practitioners of hair coloring.
2. The couplers and primary intermediates must be properly dispersed to ensure that they rapidly penetrate into the hair.
3. The dye component should have the necessary properties so that when it is mixed with the developer, the resulting mixture has the desired rheological properties. The mixture preferably is thin enough to be able to spread onto the hair, but thick enough to stay in place during the color development period. If thickened, the mixture should also be readily rinsable from the hair with water.
4. The formulations should not be irritating to the scalp.

In order to meet conditions 2 and 3 above, mixtures of surfactants, organic solvents and thickeners, are included in all commercial hair dye preparations. Typical surfactants that are used in hair color formulations are nonoxynol-2, nonoxynol-4, nonoxynol-9, octoxynbl-1, laureth-4, laureth-23, oleth-4, oleth-21, sodium lauryl sulfate, sodium lauryl ether sulfate, sodium dodecyl benzene sulfonate, sodium cocamido propylbetaine, soyatrimmonium chloride, cetyl trimmonium chloride and behenyltrimmonium chloride.

Typical organic solvents used in hair color formulations include ethyl alcohol, isopropyl alcohol, carbitol, propylene glycol and hexylene glycol.

Typical thickeners used in hair color formulations include the surfactants described above, lauric acid diethanolamide, cocamide DEA and polyacrylic acid derivatives.

DETAILED DESCRIPTION OF THE INVENTION

This invention relates to the use of certain combinations of dye intermediates together with certain dyeing vehicles. Some of the dye intermediates are known. They have been described as providing superior brightness and wear-fastness. The present inventors have discovered that, suprisingly, these dye intermediates can only be used effectively in certain dyeing vehicles. These vehicles can be distinguished by a measured quantity, the Cumulative HLB Index, which will be defined hereinafter. In order to practice the current invention the Cumulative HLB Index of the vehicle must be below a value of about 2.5.

For example, in U.S. Pat. No. 5,344,463, the combination of 3-methyl-p-aminophenol and 2-methyl-naphthol was disclosed as giving intense vibrant red shades with superior wash-fastness. All of the examples given in U.S. Pat. No.

5,344,463 consist of dye formulations in a dyeing vehicle that consists of water, ethanol and ammonia. The patent does state that solvents and surfactants may be added to the formulation up to 50% and 20% respectively. Normally, solvents and surfactants are required for good performance of a hair dye, in order to provide suitable rheology, to help wet the hair and to help remove the formulation from the hair after the dyeing is finished. Although U.S. Pat. No. 5,344,463 does teach that surfactants and solvents can be added to its compositions, it does not teach or appreciate that the nature and amount of surfactant is critical. For example, when the composition of Example 5 in U.S. Pat. No. 5,344,463 is formulated to contain 15% of Oleth-2 (an ethoxylated alcohol with a low HLB value), the color produced on hair is drastically reduced from bright red to a dull light orange color. By comparison when these dyes are formulated, in accordance with the present invention, in a composition such that the Cumulative HLB Index is 2.5, vivid and fade-resistant colors are enabled.

In U.S. Pat. No. 4,507,280, the patentees disclose that solvents and surfactants interfere with the dyeing of oxidation dyes, and that dyeing can be effected with lower levels of dye in a highly aqueous base with low concentrations of solvent and surfactant. However, U.S. Pat. No. 4,507,280 does not disclose or suggest that there are differences between surfactants and that some surfactants have a lesser effect on dyeing than others. Also, U.S. Pat. No. 4,507,280 does not teach or suggest that some dye intermediates, are more affected than others by the nature and concentration of the surfactants in the dyeing vehicle. Although the dyes specified in U.S. Pat. No. 4,507,280 are more efficient at dyeing in a highly aqueous base, they can be used in other vehicles to provide a full range of shades. This includes vehicles typical of those used in commercial hair color products that generally contain quantities of low HLB surfactants.

The dyes disclosed in U.S. 5,344,463, which are shown in Formulas I and II as well as the primary intermediates shown in Formula III, are greatly affected by surfactants. They give very weak colors when used in vehicles containing quantities of low HLB surfactants.

The present inventors have found that, suprisingly, in order to make optimal use of the oxidation dyes summarized by Formula I, II and III, the dyeing vehicle must have certain properties. The characteristics of the vehicle that are essential to securing the benefits of the present invention include the amount of water, organic solvents and the nature of the surfactants in the composition. We will define a quantity that we call the 'Cumulative HLB Index' of the final composition as it is applied to the hair. The usefulness of a vehicle for dyeing with the intermediates of U.S. Pat. No. 5,344,463 can be determined from the 'Cumulative HLB Index' of the final dye formulation.

The 'Cumulative HLB Index' is defined as the sum of the HLB Indexes of each ingredient in the formulation. HLB is a concept well known and understood by the skilled artisan. It is an expression of the relative simultaneous attraction of a material, particularly a surfactant, for water and oil. A surfactant having a high HLB is considered hydrophilic. A surfactant having a low HLB is considered lipophilic.

The HLB of a surfactant can be calculated in several different ways, but for the purposes of this invention, the HLB index of the ingredients of a composition is calculated from the Hildebrand Solubility Parameters ($\partial/\text{Mpa}^{1/2}$) according to the following equation, as outlined in the *CRC Handbook of Solubility Parameters and Other Cohesion Parameters*, Barton, Allan F. M., CRC Press (1983):

$$HLB = \left( \frac{\partial/\text{MPa}^{1/2} - 16.8}{\partial/\text{MPa}^{1/2} - 12.3} \right) \times 54$$

The values for the Hildebrand Solubility Parameters were taken from Barton. The HLB values that are calculated from this equation do not always agree with values calculated by other methods, but the present inventors found that they work particularly well for the purpose of predicting whether a particular dye vehicle is suitable for the practice of the present invention.

'HLB Index' of an ingredient is calculated by dividing its formula weight percent by its HLB. Thus, the Cumulative HLB Index would be equal to Wt % of ingredient 1/HLB value of ingredient 1+Wt % of ingredient 2/HLB value of ingredient 2+Wt % of ingredient 3/HLB value of ingredient 3, etc., etc., etc.

The following is an example of how the Cumulative HLB Index is calculated for a composition containing water, Surfactant A and Surfactant B.

| Ingredients | Wt % | HLB value of the ingredient |
|---|---|---|
| Water | 80 | 47 |
| Surfactant A | 15 | 20 |
| Surfactant B | 5 | 10 |

Thus, the 'Cumulative HLB Index'=80/47+15/20+5/10= 1.7+0.75+0.5=2.95.

All components in a formulation contribute to the Cumulative HLB Index, however, when there are many ingredients in a formula, it may be acceptable to exclude some ingredients that are at very low concentrations, as they will have a negligible effect on the calculated result. For example, a preservative with an HLB of 1 at a concentration of 0.02% would increase the HLB index by only 0.02 units. Eliminating this calculation would save a great deal of time, since the HLB or the Hildebrand Solubility Parameter of the preservative might not be known.

Although the HLB values calculated using the above equation may be slightly different than the HLB values calculated by other means, the concept is the same, and is well known and understood by the skilled artisan.

With the novel compositions of this invention, the Cumulative HLB Index will be up to about 2.5, although useful results can be obtained with somewhat higher values. This can be seen in FIG. 1, wherein CIE a* value (in other words red intensity) is plotted against Cumulative HLB Index for a series of compositions using the dye intermediates of Examples 1. It should be noted that when the CIE a* value is higher than about 14, indicated by a dashed line in the figure, the hair appears to be an intense red shade. When the CIE a* value is below about 13.5 the color of the hair is a reddish brown and the color does not appear to be very saturated. In FIG. 1, it can be seen that the red intensity decreases as the Cumulative HLB Index increases. The CIE a* value decreases quite rapidly until the Cumulative HLB Index is about 2.8, by which point the CIE a* value is well below 14. The Cumulative HLB Index must be below about 2.5 in order to obtain the benefits of the present invention.

When the Cumulative HLB Index of the dyeing vehicle is significantly higher than 2.5, it may be possible to get some color from the dyes of the current invention, specifically those defined by Formula I, II and III below. However, the dyeing will be very weak and will not allow formulation of a range of shades.

The novel oxidation dye formulations that are the subject of this invention contain one or more of the following intermediates:

The novel oxidation dye formulations that are the subject of this invention contain one or more of the following intermediates:

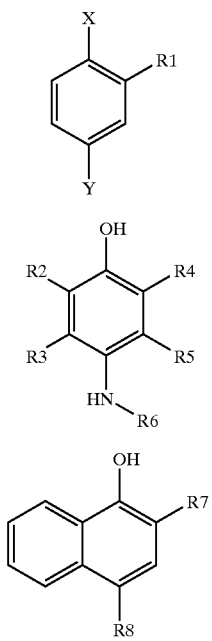

In which $R_1$ is a $C_2$–$C_6$ alkyl group or a $C_2$–$C_6$ alkyl group substituted with one or more hydroxyl groups, $R_2$ denotes a $C_1$–$C_6$ alkyl group or a $C_1$–$C_6$ alkyl group substituted with at least one hydroxyl group, $R_3$, $R_4$, $R_5$, $R_6$, $R_7$ and $R_8$ are hydrogen, $C_1$–$C_6$ alkyl or hydroxyalkyl with the restriction that at least one of $R_3$ and $R_5$ must be hydrogen and X and Y are amino or hydroxyl groups with the restriction that, if one of X and Y is a hydroxyl group, the other is an amino group and with the further provision that when the primary intermediate is a compound of formula II, the coupler is a compound of formula III.

We have suprisingly found that, when these intermediates are used with a dyeing medium having a Cumulative HLB Index lower than about 2.5, intense, wear-stable colors are obtained.

As in the production of other oxidative dye compositions, other couplers or primary intermediates may be added to alter the improved color. These compounds, as the skilled artisan will recognize, may be selected from a wide variety of couplers and primary intermediates well known to those skilled in the art. As primary intermediates, there may be mentioned by way of example, p-phenylenediamine, p-toluenediamine, 2-chloro-p-phenylenediamine, 2-methoxy-p-phenylenediamine, p-aminophenol and N,N-bis(2-hydroxy-ethyl)-p-phenylenediamine. Examples of couplers that may be added to the intermediates that are the subject of the current invention include m-phenylenediamine, m-aminophenol, 2-methyl-5-aminophenol, 1-naphthol, resorcinol and 2-methylresorcinol. The salts of the foregoing compounds, especially the acid salts such as the monohydrochlorides, the dihydrochlorides or the corresponding sulfuric acid salts, may also be employed.

Other conventional agents often employed in hair coloring compositions may be employed in the dye component or in the developer component. These include, for example, fragrances, coloring agents and chelating agents.

Antioxidants, such as sodium sulfite, erythorbic acid and ascorbic acid, may also be included to inhibit premature oxidation.

Although the dye composition of the invention has been described heretofore as containing the developer so that the oxidative hair dye is produced, the developer can, as is usually the case, be a separate composition, which is mixed with the dye precursors just prior to use. When this is done, the amount of water in the developer composition and in the composition containing the dye precursors and the Cumulative HLB index of the final composition should be such that the final composition produced by mixing the developer composition and dye precursor composition meets the requirements set forth previously herein for the final dye composition so that the benefits of the invention are obtained.

The dye and developer components of the compositions of this invention may be prepared in any of the usual formats, such as liquids, lotions, gels and the like. It is of course important that the compositions applied to the hair have and maintain sufficient viscosity to stay on the hair during the coloring procedure.

It is desirable, but not essential, that the viscosities of the dye and developer components be close to each other. If the difference in viscosities is too great they will be difficult to mix. On shaking, the thinner component will aggregate and the rate of blending will be retarded. Typically, the viscosities of the components and of the final compositions will be from about 1000 to 25,000 cps.

The essence of the present invention is the discovery of a limited class of coupler/primary intermediate combinations which in aqueous oxidative dye compositions having the essential characteristics described herein can be employed to dye hair and impart highly desirable colors which manifest unexpectedly improved wash fastness and resistance to light fading compared to hair coloration achievable with conventional oxidative hair coloring compositions and/or permit more intense vivid dyeouts to be obtained.

The total amount of coupler in the oxidative dye compositions of this invention is from about 0.01% to 10%, preferably 0.05% to 5%. This is the same amount of coupler normally employed with conventional oxidative dye compositions. If an auxiliary coupler is employed, from about 0.01% to 3%, preferably 0.01% to 1.5%, will be a coupler represented by formula III.

The amount of primary intermediate in the final compositions will be the amount normally employed, i.e., from about 0.01% to 10%, preferably 0.1% to 5%. If an auxiliary primary intermediate is employed from about 0.01% to 3%, preferably 0.01% to 1.5%, will be a primary intermediate represented by formula I or formula II.

A wide variety of surfactants and surfactant mixtures may be employed in the practice of this invention. Several typically useful surfactants are set forth below. They may be used singly or in blends containing at least two of them. Useful surfactants include amphoteric surfactants such as betaines, sultaines, glycinates, proprionates; alkylpolyglycosides; fatty acid soaps such as alkanolamine, alkali metal or alkaline earth metal salts of a carboxylic acid containing from about 11 to 19 carbon atoms; higher alkylbenzene sulfonates; alkyl-naphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures. Illustrative of specific surfactants that can be used are sodium lauryl sulfate; polyoxyethylene lauryl ether: myristyl sulfate; glyceryl monostearate; triethanolamine oleate, sodium salt of palmitic methyl taurine; cetyl pyridinium chloride; lauryl sulfonate; myristyl sulfonate; lauric diethanolamide; polyoxyethylene stearate; ethoxylated oleoyl diethanolamide; stearyldimethyl benzyl ammonium chloride; dodecylbenzene sodium sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate; the sodium salt of 3-diethyl tridecanol-6-sulfate and the like.

If a thickening agent is employed to control the viscosity of the composition, two classes of these products have been found to be useful. One is a modified polyurethane of which several are available. They are sold under the trade names Aculyn 44® and Aculyn 46® (Rohm & Haas) 46. These are also known as C18 polycarbamyl polyglycol ester. The other type of thickener that has been found useful is a hydrophobically modified polyacrylic acid. Examples are steareth-10 alkyl ether/acrylate polymer (Aculyn 22® from Rohm & Haas), acrylates copolymer (Aculyn 33® from Rohm & Haas), steareth-10 allyl ether/acrylate copolymer (Salcare SC80® from Allied Colloids) and Acrylates/Ceteth-20 Itaconate Copolymer (Structure 3000® from National Starch)

Any of a wide variety of alkaline reagents may be employed with the modified polyacrylic acids. Because of its freedom from toxicity over a wide concentration range and its economy, ammonium hydroxide is an acceptable alkalizing agent. However, any other compatible ammonia derivative can be used in place of, or together with, ammonium hydroxide to effect the desired alkalinity. For example, an alkylamine such as ethylamine, or triethylamine; or alkanolamines, such as ethanolamine, diethanolamine, aminomethyl propanol, aminomethyl propanediol and trishydroxymethyl aminomethane may be employed. Likewise, any other of the organic or inorganic alkalizing agents may be used, such as sodium or potassium hydroxide, sodium or potassium carbonate, sodium phosphate, sodium hydrogen phosphate, sodium silicate, guanidine hydroxide and the like. The preferred alkaline reagents are ammonium hydroxide, sodium carbonate and ethanolamine.

When the alkaline reagents listed above, or their equivalents, are employed at a concentration of from about 0.5% to 10%, the pH of the dye component will be from about 8 to 10.5.

Although they are not essential, buffering agents may be employed to stabilize the pH of the dye component during storage. Typically useful buffers include ammonium and alkali metal phosphates, bicarbonates, carbonates and, to a lesser extent, borates. Also suitable are amino buffers such as, N-[2-hydroxyethyl]-piperazine-$N^1$-[2-ethanesulfonic acid](HEPES), N-[2-acetamido]-2-aminoethane sulfonic acid (ACES), tris[-hydroxymethyl]aminomethane (TRIS) and N-tris[hydroxymethyl]-methyl-3-aminopropane sulfonic acid (TAPS). The ammonium and alkali metal carbonates are also suitable. The preferred buffers are. TRIS, sodium and potassium carbonate, bicarbonate and phosphate.

The dye component and the developer can be combined by mixing them directly on the hair of the user. If they are mixed on the hair, adding the dye component first is preferable. It is, preferred to mix them in a mixing vessel for subsequent application to the hair.

The present invention also encompasses a kit comprising at least two containers, one containing the dye component, the other the developer component, the two when mixed forming a composition of the present invention.

The method of the invention comprises applying the oxidative dye composition of the present invention to the hair to be colored and allowing it to remain in contact with the hair until the desired hair color has been attained after which the composition is removed from the hair by rinsing.

Some typical examples of dye components and developer components are shown in Tables 1 and 2 which follow. Each of the components was mixed using conventional procedures. Table 1 records the color results on gray hair when a dye component of Table 1 was mixed with a developer of Table 2 in a 1 to 1 ratio, and the resultant dye composition was applied to human hair for 30 minutes employing the usual procedures for human hair dyeing.

TABLE I

EXAMPLES OF DYE FORMULATIONS

|  | Example 1 | Example 2 | Example 3 | Example 4 | Example 5 |
|---|---|---|---|---|---|
| Cocamidopropyl betaine | 7.00 |  |  |  | 7.00 |
| Cocamphocarboxyglycinate |  | 7.00 |  | 7.00 |  |
| Cocoamphodipropionate |  |  | 7.00 |  |  |
| Oleic acid | 5.00 | 5.00 |  | 5.00 | 5.00 |
| Lauric acid |  |  | 5.00 |  |  |
| Octylpolyglycoside | 5.00 |  |  | 8.00 |  |
| Decylpolyglycoside |  | 8.00 |  |  | 8.00 |
| Dodecylpolyglycoside |  |  | 5.00 |  |  |
| Ammonium hydroxide | 5.00 | 5.00 |  | 5.00 |  |
| Monoethanolamine |  |  | 3.00 |  |  |
| Aminoethylpropanol |  |  | 3.00 |  |  |
| Sodium carbonate |  |  |  |  | 2.50 |
| Sodium bicarbonate |  |  |  |  | 0.50 |
| Sodium citrate |  |  |  |  | 0.50 |
| EDTA | 0.10 | 0.10 | 0.10 | 0.10 | 0.10 |
| Sodium sulfite | 0.10 | 0.10 | 0.10 | 0.10 | 0.10 |
| Fragrance | 0.50 | 0.50 | 0.50 | 0.50 | 0.50 |
| 1-acetoxy-2-methyl-naphthalene | 1.20 |  |  | 0.20 | 0.50 |
| 2-methyl-1-naphthol |  | 0.20 |  |  |  |
| 4-methoxy-2-methyl-1-naphthol |  |  | 1.20 |  |  |

TABLE I-continued

EXAMPLES OF DYE FORMULATIONS

|  |  |  |  |  |  |
|---|---|---|---|---|---|
| 4-amino-2-hydroxytoluene | 0.60 |  |  | 0.10 | 0.10 |
| 2-methyl-5-hydroxyethylaminophenol |  | 0.40 |  |  |  |
| 2-methyl-5-ethoxyethylaminophenol |  |  | 0.20 |  |  |
| p-aminophenol | 1.00 |  |  | 0.30 | 0.40 |
| 3-methyl-p-aminophenol |  | 0.30 |  |  |  |
| 1-[(2-hydroxy-5-amino)phenyl]-1,2-ethanediol |  |  | 1.20 |  |  |
| p-phenylenediamine |  |  | 0.10 |  | 0.50 |
| N,N-bis(2-hydroxyethyl)-p-phenylenediamine | 0.50 | 0.02 |  |  |  |
| 1-(2,5-diaminophenyl)-1,2-ethanediol |  |  |  | 0.10 |  |
| Water | qs to 100 | qs to 100 | qs to 100 | qs to 100 | qs to 100 |
| Developer Used | 1 | 1 | 2 | 3 | 4 |
| Cumulative HLB Index | 2.36 | 2.36 | 2.36 | 2.41 | 2.49 |
| Color results on gray hair: | Dk burgundy | Lt burgundy | Bright red | Copper red | Red brn |

|  | Example 6 | Example 7 | Example 8 | Example 9 | Example 10 |
|---|---|---|---|---|---|
| Cocamidopropyl betaine | 7.00 |  |  |  | 7.00 |
| Cocamphocarboxyglycinate |  | 7.00 |  | 7.00 |  |
| Cocoamphodipropionate |  |  | 7.00 |  |  |
| Oleic acid | 5.00 | 5.00 |  | 5.00 | 5.00 |
| Lauric acid |  |  | 5.00 |  |  |
| Octylpolyglycoside | 5.00 |  |  | 8.00 |  |
| Decylpolyglysoside |  | 8.00 |  |  | 8.00 |
| Dodecylpolyglycoside |  |  | 5.00 |  |  |
| Ammonium hydroxide | 5.00 | 5.00 |  | 5.00 |  |
| Monoethanolamine |  |  | 3.00 |  |  |
| Aminoethylpropanol |  |  | 3.00 |  |  |
| Sodium carbonate |  |  |  |  | 2.50 |
| Sodium bicarbonate |  |  |  |  | 0.50 |
| Sodium citrate |  |  |  |  | 0.50 |
| EDTA | 0.10 | 0.10 | 0.10 | 0.10 | 0.10 |
| Sodium sulfite | 0.10 | 0.10 | 0.10 | 0.10 | 0.10 |
| Fragrance | 0.50 | 0.50 | 0.50 | 0.50 | 0.50 |
| 1-acetoxy-2-methyl-naphthalene |  |  |  | 0.20 | 0.50 |
| 2-methyl-1-naphthol | 0.60 | 0.20 |  |  |  |
| 4-methoxy-2-methyl-1-naphthol |  |  | 1.20 |  |  |
| m-phenylenediamine | 0.02 |  |  | 0.10 | 0.10 |
| N,N-bis(2-hydroxyethyl)-m-phenylenediamine |  | 0.40 |  |  |  |
| 4-(N-ethyl-N-2-hydroxyethyl)-2-methyl-m-phenylenediamine |  |  | 0.20 |  |  |
| p-aminophenol |  |  |  | 0.30 | 0.40 |
| 3-methyl-p-aminophenol | 0.50 | 0.30 |  |  |  |
| 1-[(2-hydroxy-5-amino)phenyl]-1,2-ethanediol |  |  | 1.20 |  |  |
| p-phenylenediamine | 0.15 |  | 0.10 |  | 0.50 |
| N,N-bis(2-hydroxyethyl)-p-phenylenediamine |  | 0.02 |  |  |  |
| 1-(2,5-diaminophenyl)-1,2-ethanediol |  |  |  | 0.1 |  |
| Water | qs to 100 | qs to 100 | qs to 100 | qs to 100 | qs to 100 |
| Developer Used | 2 | 3 | 4 | 5 | 5 |
| Cumulative HLB Index | 2.39 | 2.41 | 2.46 | 2.5 | 2.53 |
| Color results on gray hair: | Dk burgundy | burgundy | Dk auburn | Auburn brn | Burgundy brn |

|  | Example 11 | Example 12 | Example 13 | Example 14 | Example 15 |
|---|---|---|---|---|---|
| Cocamidopropyl betaine | 7.00 |  |  |  | 7.00 |
| Cocamphocarboxyglycinate |  | 7.00 |  | 7.00 |  |
| Cocoamphodipropionate |  |  | 7.00 |  |  |
| Oleic acid | 5.00 | 5.00 |  | 5.00 | 5.00 |
| Lauric acid |  |  | 5.00 |  |  |
| Octylpolyglycoside | 5.00 |  |  | 8.00 |  |
| Decylpolyglysoside |  | 8.00 |  |  | 8.00 |
| Dodecylpolyglycoside |  |  | 5.00 |  |  |
| Ammonium hydroxide | 5.00 | 5.00 |  | 5.00 |  |
| Monoethanolamine |  |  | 3.00 |  |  |
| Aminoethylpropanol |  |  | 3.00 |  |  |
| Sodium carbonate |  |  |  |  | 2.50 |
| Sodium bicarbonate |  |  |  |  | 0.50 |
| Sodium citrate |  |  |  |  | 0.50 |
| EDTA | 0.10 | 0.10 | 0.10 | 0.10 | 0.10 |
| Sodium sulfite | 0.10 | 0.10 | 0.10 | 0.10 | 0.10 |
| Fragrance | 0.50 | 0.50 | 0.50 | 0.50 | 0.50 |
| 1-acetoxy-2-methyl-naphthalene | 1.20 |  |  | 0.20 | 0.50 |
| 2-methyl-1-naphthol |  | 0.20 |  |  |  |

TABLE I-continued

EXAMPLES OF DYE FORMULATIONS

|  | Ex. 11 | Ex. 12 | Ex. 13 | Ex. 14 | Ex. 15 |
|---|---|---|---|---|---|
| 4-methoxy-2-methyl-1-naphthol |  |  | 1.20 |  |  |
| Resorcinol | 0.60 |  |  | 0.10 | 0.10 |
| m-aminophenol |  | 0.40 |  |  |  |
| 3-amino-m-cresol |  |  | 0.20 |  |  |
| p-aminophenol | 1.00 |  |  | 0.30 | 0.40 |
| 3-methyl-p-aminophenol |  | 0.30 |  |  |  |
| 1-[(2-hydroxy-5-amino)phenyl]-1,2-ethanediol |  |  | 1.20 |  |  |
| p-phenylenediamine |  |  | 0.10 |  | 0.50 |
| N,N-bis(2-hydroxyethyl)-p-phenylenediamine | 0.50 | 0.02 |  |  |  |
| 1-(2,5-diamino-phenyl)-1,2-ethanediol |  |  |  | 0.10 |  |
| Water | qs to 100 | qs to 100 | qs to 100 | qs to 100 | qs to 100 |
| Developer Used | 1 | 3 | 5 | 2 | 4 |
| Cumulative HLB Index | 2.36 | 2.41 | 2.5 | 2.37 | 2.49 |
| Color results on gray hair: | Dk auburn | Brght Copper Brn | Auburn | Copper brn | Warm ash brn |

|  | Example 16 | Example 17 | Example 18 | Example 19 | Example 20 |
|---|---|---|---|---|---|
| Oleth-21 | 3.00 | 2.00 |  |  |  |
| Laureth-23 |  |  | 2.00 | 2.50 | 4.00 |
| Soytrimonnium Chloride | 1.00 |  | 2.00 |  | 2.00 |
| Oleic acid | 4.50 | 2.00 | 1.20 | 1.50 | 2.00 |
| Decylpolyglycoside | 2.00 | 2.50 |  | 1.00 |  |
| Ammonium hydroxide (28%) | 5.00 |  | 4.90 | 5.00 | 8.00 |
| C18 Polycarbamyl Polyglycol Ester | 1.20 | 1.50 | 1.00 | 1.30 | 1.10 |
| Lauramide DEA |  |  | 0.90 | 1.50 |  |
| Fragrance | 0.20 | 0.50 | 0.24 | 0.10 | 0.30 |
| Monoethanolamine |  | 6.00 |  |  |  |
| p-Phenylenediamine | 0.50 | 0.05 |  |  | 0.60 |
| Resorcinol | 0.45 | 0.40 | 0.80 | 1.10 | 0.35 |
| N,N-bis(2-hydroxyethyl)-p-phenylenediamine | 0.20 | 0.02 |  |  |  |
| 1-(2,5-diaminophenyl)-1,2-ethanediol |  |  | 1.40 | 1.30 |  |
| m-aminophenol |  | 0.10 | 0.34 | 0.30 |  |
| m-phenylenediamine | 0.20 |  | 0.10 | 0.20 |  |
| 2-Methyl-1-Naphthol |  |  |  | 0.50 | 0.70 |
| 3-Methyl-4-Aminophenol |  |  |  | 0.80 | 0.90 |
| Developer Used | 7 | 7 | 7 | 7 | 6 |
| Cumulative HLB Index | 2.3 | 0.37 | 2.35 | 2.16 | 2.2 |
| Color Result | Med Brown | Lt Blonde | Med Gold Brwn | Warm Brown | Rich Auburn |

TABLE II

EXAMPLES OF DEVELOPERS

|  | Example 1 | Example 2 | Example 3 | Example 4 | Example 5 | Example 6 | Example 7 |
|---|---|---|---|---|---|---|---|
| Hydrogen peroxide | 3.00 | 6.00 | 9.00 | 3.00 | 6.00 | 6.00 | 6.00 |
| Acrylates Copolymer | 1.50 | 1.50 | 2.50 | 1.00 | 3.50 |  |  |
| Acrylates/steareth-20 Methacrylate Copolymer | 1.50 | 1.50 | 1.50 | 5.00 | 3.50 |  |  |
| EDTA | 0.10 | 0.10 | 0.10 | 0.10 | 0.10 |  |  |
| Phosphoric acid | 0.10 | 0.10 | 0.10 | 0.10 | 0.10 | 0.07 | 0.12 |
| Nonoxynol-9 |  |  |  |  |  | 1.50 |  |
| Nonoxynol-4 |  |  |  |  |  | 1.00 |  |
| Oleth-4 |  |  |  |  |  |  | 2.20 |
| Oleth-21 |  |  |  |  |  |  | 2.20 |
| Water | 93.80 | 90.80 | 86.80 | 90.80 | 86.80 | 91.43 | 89.48 |

What is claimed is:

1. An aqueous oxidative hair dye composition for application to hair comprising:

(a) at least one primary intermediate;

(b) at least one coupler;

(c) an oxidizing agent;

(d) an organic solvent;

(e) a thickening agent selected from the group consisting of a mixture of surfactants, polyurethanes, and polyacrylic acid derivatives and mixtures thereof, said thickening agent being present in the composition to provide a viscosity of from about 1,000 to about 25,000 cps; and (f) water, said composition containing at least one of:

(1) as the at least one primary intermediate (a), the compound of formula I:

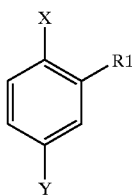

wherein $R_1$ is a $C_2$–$C_6$ alkyl group or a $C_2$–$C_6$ alkyl group in which one or more of the hydrogen atoms is replaced by a hydroxyl and X and Y are independently hydroxyl or amino groups, provided that if one of X and Y is hydroxyl, the other is amino, or (2) as the at least one coupler (b), the coupler compound of formula III:

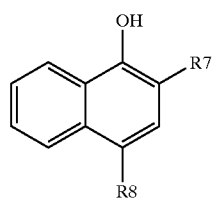

where $R_7$ and $R_8$ are independently hydrogen, $C_1$–$C_6$ alkyl or hydroxyalkyl, provided that one of $R_7$ and $R_8$ must be other than hydrogen, said hair dyeing composition having a cumulative HLB Index of less than about 2.5.

2. The composition of claim 1 wherein the composition contains the compound of formula I present in an amount of from about 0.01% to about 10% by weight of the composition.

3. The composition of claim 2 wherein $R_1$ is a $C_2$–$C_6$ alkyl group in which one of the hydrogen atoms is replaced by a hydroxyl, and X is hydroxyl.

4. The composition of claim 1 wherein the composition contains the compound of formula III present in an amount of from about 0.01 to about 10% by weight of the composition.

5. The composition of claim 4 wherein $R_7$ is methyl and $R_8$ is hydrogen.

6. The composition of claim 1 further comprising (i) a primary intermediate selected from the group consisting of p-phenylene-diamine, p-toluenediamine, p-aminophenol, 3-methyl-p-aminophenol, and N,N-bis(2-hydroxyethyl)-p-phenylenediamine, and (ii) a coupler selected from the group consisting of m-phenylenediamine, m-aminophenol, 2-methyl-5-aminophenol 1-naphthol, resorcinol, and 2-methyl resorcinol.

7. The composition of claim 4 wherein the composition further contains 3-methyl-p-aminophenol.

8. The composition of claim 3 further comprising as the coupler (b), the coupler compound of formula III.

9. The composition of claim 1 wherein the thickening agent is a polyacrylic acid derivative.

10. The composition of claim 1 wherein the thickening agent is a polyurethane.

11. The composition of claim 1 wherein the oxidizing agent is hydrogen peroxide.

12. The composition of claim 7 wherein the oxidizing agent is hydrogen peroxide.

13. A method for the oxidative dyeing of hair comprising contacting the hair with a tinctorially effective amount of a hair dye composition in accordance with claim 1 for a time sufficient to dye the hair.

14. The method of claim 13 wherein the hair dye composition contains the compound of formula III present in an amount of from about 0.01 to about 10% by weight of the composition.

15. The composition of claim 8 in which $R_7$ is methyl and $R_8$ is hydrogen.

16. The method of claim 14 wherein the thickening agent is a polyacrylic acid derivative.

17. The method of claim 14 wherein the thickening agent is a polyurethane.

18. The method of claim 14 wherein the compound of formula III is 2-methyl-1-naphthol and wherein the composition further contains 3-methyl-p-aminophenol.

* * * * *